United States Patent
Pye et al.

(10) Patent No.: US 7,341,450 B2
(45) Date of Patent: Mar. 11, 2008

(54) TOOTH SHADE SCAN SYSTEM AND METHOD

(75) Inventors: Graham Pye, Genk (BE); Harald Kerschbaumer, Klaus (AT)

(73) Assignees: Shade Analyzing Technologies, Inc., Darien, CT (US); Ivoclar Vivadent AG, Schaan (LI)

( * ) Notice: Subject to any disclaimer, the term of this patent is extended or adjusted under 35 U.S.C. 154(b) by 746 days.

(21) Appl. No.: 10/678,543

(22) Filed: Oct. 3, 2003

(65) Prior Publication Data

US 2005/0074718 A1 Apr. 7, 2005

(51) Int. Cl.
*A61C 19/04* (2006.01)
*G01J 3/51* (2006.01)

(52) U.S. Cl. .......... 433/29; 356/402; 356/406

(58) Field of Classification Search .......... 433/26, 433/203.1; 356/402, 405, 406, 407, 408
See application file for complete search history.

(56) References Cited

U.S. PATENT DOCUMENTS

| | | | |
|---|---|---|---|
| 3,861,044 A | 1/1975 | Swinson, Jr. ............ | 32/17 |
| 3,975,760 A | 8/1976 | Yamanaka et al. ......... | 348/262 |
| 3,986,777 A | 10/1976 | Roll ...................... | 356/176 |
| 4,016,598 A | 4/1977 | Yamanaka ................ | 358/41 |
| 4,106,056 A | 8/1978 | Nagumo et al. .......... | 35/50 |
| 4,247,202 A | 1/1981 | Failes .................. | 356/310 |
| 4,414,635 A | 11/1983 | Gast et al. ............ | 364/526 |
| 4,518,258 A | 5/1985 | Broersma ............... | 356/405 |
| 4,547,074 A | 10/1985 | Hinoda et al. .......... | 356/405 |
| 4,575,805 A | 3/1986 | Moermann et al. ...... | 700/163 |
| 4,591,900 A | 5/1986 | Heeb et al. ........... | 358/44 |
| 4,616,933 A | 10/1986 | Leveque et al. ........ | 356/416 |
| 4,623,973 A | 11/1986 | Hoffrichter et al. .... | 364/526 |
| 4,654,794 A | 3/1987 | O'Brien ............... | 433/215 |

(Continued)

FOREIGN PATENT DOCUMENTS

DE 19534517 9/1995

(Continued)

OTHER PUBLICATIONS

Benson (ed.), Visual Information Transmission, Television Engineering Handbook, pp. 4.3-4.76 (1986, McGraw-Hill).

(Continued)

*Primary Examiner*—Ralph A. Lewis
(74) *Attorney, Agent, or Firm*—Winston & Strawn LLP

(57) ABSTRACT

A tooth shade scan system is provided that identifies tooth shades for a patient's tooth. An electronic database of tooth shade information for a shade guide may be stored. The database may include shade information based on tooth regions (e.g., the incisal, central, and cervical). A system operator may be shown an image of a patient's tooth on display equipment such as a computer monitor. An application running on the system may display dividers that the operator can manipulate to divide the image of the patient's tooth into regions. The regions may correspond to regions for which specific tooth shade information is available in the database. Values representative of a limited number of color characteristics for a region as a whole may be determined from the image. Corresponding categories of color characteristics may exist in the database, which is then used to identify tooth shades by region for the patient's tooth.

14 Claims, 6 Drawing Sheets

U.S. PATENT DOCUMENTS

| | | | |
|---|---|---|---|
| 4,692,481 A | 9/1987 | Kelly | 523/210 |
| 4,813,000 A | 3/1989 | Wyman et al. | 382/165 |
| 4,836,674 A | 6/1989 | Lequime et al. | 356/319 |
| 4,881,811 A | 11/1989 | O'Brien | 356/323 |
| 4,903,122 A | 2/1990 | Ozaki et al. | 358/48 |
| 4,919,617 A | 4/1990 | Antons et al. | 433/26 |
| 4,978,296 A | 12/1990 | Antons et al. | 433/26 |
| 5,012,431 A | 4/1991 | Stanziola | 382/162 |
| 5,027,138 A | 6/1991 | Gandrud | 348/66 |
| 5,124,797 A | 6/1992 | Williams et al. | 348/340 |
| 5,177,694 A | 1/1993 | Graham et al. | 382/165 |
| 5,231,472 A | 7/1993 | Marcus et al. | 356/402 |
| 5,240,414 A | 8/1993 | Thompson | 433/26 |
| 5,273,429 A | 12/1993 | Rekow et al. | 433/215 |
| 5,282,025 A | 1/1994 | Sato | 348/273 |
| 5,313,267 A | 5/1994 | MacFarlene et al. | 356/405 |
| 5,340,309 A | 8/1994 | Robertson | 433/69 |
| 5,373,364 A | 12/1994 | Krzyminski | 356/405 |
| 5,383,020 A | 1/1995 | Vieillefosse | 356/405 |
| 5,430,811 A | 7/1995 | Fukushima et al. | 381/254 |
| 5,431,562 A | 7/1995 | Andreiko et al. | 433/25 |
| 5,434,604 A | 7/1995 | Cleary et al. | 347/19 |
| 5,452,219 A | 9/1995 | Dehoff et al. | 364/474.05 |
| 5,453,009 A | 9/1995 | Feldman | 433/215 |
| 5,498,157 A | 3/1996 | Hall | 433/26 |
| 5,549,476 A | 8/1996 | Stern | 433/233 |
| 5,587,912 A | 12/1996 | Andersson et al. | 433/215 |
| 5,685,712 A | 11/1997 | Fischer | 433/26 |
| 5,690,486 A | 11/1997 | Zigelbaum | 433/29 |
| 5,692,900 A | 12/1997 | Fischer | 433/26 |
| 5,725,372 A | 3/1998 | Leon | 433/26 |
| 5,733,126 A | 3/1998 | Andersson et al. | 433/233 |
| 5,745,229 A | 4/1998 | Jung et al. | 356/73 |
| 5,759,030 A | 6/1998 | Jung et al. | 433/29 |
| 5,798,839 A | 8/1998 | Berner et al. | 356/402 |
| 5,823,778 A | 10/1998 | Schmitt et al. | 433/214 |
| 5,851,113 A | 12/1998 | Jung et al. | 433/29 |
| 5,851,115 A | 12/1998 | Carlsson et al. | 433/215 |
| 5,871,351 A | 2/1999 | Jung et al. | 433/26 |
| 5,880,826 A | 3/1999 | Jung et al. | 356/73 |
| 5,938,446 A | 8/1999 | Andersson et al. | 433/25 |
| 6,008,905 A | 12/1999 | Breton et al. | 356/402 |
| 6,030,209 A | 2/2000 | Panzera et al. | 433/26 |
| 6,038,024 A | 3/2000 | Berner | 356/326 |
| 6,058,357 A | 5/2000 | Granger | 702/104 |
| 6,111,650 A | 8/2000 | Rawicz et al. | 56/402 |
| 6,132,210 A | 10/2000 | Lehmann | 433/26 |
| 6,244,863 B1 | 6/2001 | Rawicz et al. | 433/26 |
| 6,305,933 B1 | 10/2001 | Lehmann | 433/26 |
| 6,331,113 B1 | 12/2001 | Morris et al. | 433/215 |
| 6,358,047 B2 | 3/2002 | Lehmann | 433/26 |
| 6,384,917 B1 | 5/2002 | Fradkin | 356/402 |
| 6,561,800 B2 | 5/2003 | Lehmann | 433/26 |
| 6,575,751 B1 | 6/2003 | Lehmann et al. | 433/223 |

FOREIGN PATENT DOCUMENTS

| | | |
|---|---|---|
| EP | 036 0657 | 3/1990 |
| JP | 64-052455 | 2/1989 |
| JP | 01052454 | 2/1989 |
| JP | 4301530 | 10/1992 |
| JP | 4338465 | 11/1992 |
| WO | WO 86 03292 | 6/1986 |
| WO | WO 91 02955 | 3/1991 |
| WO | WO 95 15731 | 6/1995 |

OTHER PUBLICATIONS

Internet Search for "Prosthodontics" (Jun. 2001).
http://cortexmachina.com/products/e_shadescan.htm, Jun. 2001.
www.issaquah-dl.com/, Jun. 2001.
http://www.mht.ch/mhtint/spectro.htm, Jun. 2001.
http://www.xrite.com/product_overview.aspx?Line=13, Jun. 2001.

PATIENT'S TOOTH

| | R | B | G | L* | a* | b* |
|---|---|---|---|---|---|---|
| INCISAL | 3.5 | 1.0 | 5.0 | 3.2 | 2.2 | 5.5 |
| CENTRAL | 2.2 | 1.5 | 5.5 | 1.3 | 0.7 | 5.7 |
| CERVICAL | 4.2 | 2.0 | 2.2 | 0.1 | 1.3 | 5.0 |

70

COMPARE TO DATABASE

72

| | R | B | G | L* | a* | b* | |
|---|---|---|---|---|---|---|---|
| SHADE 1 | $R_1$ | $B_1$ | $G_1$ | $L^*_1$ | $a^*_1$ | $b^*_1$ | |
| SHADE 2 | $R_2$ | $B_2$ | $G_2$ | $L^*_2$ | $a^*_2$ | $b^*_2$ | |
| ⋮ | | | | | | | INCISAL |
| SHADE N | | | | | | | |
| SHADE 1 | | | | | | | |
| SHADE 2 | | | | | | | |
| ⋮ | | | | | | | CENTER |
| SHADE N | | | | | | | |
| SHADE 1 | | | | | | | |
| SHADE 2 | | | | | | | |
| ⋮ | | | | | | | CERVICAL |
| SHADE N | | | | | | | |

Fig. 6

TOOTH SHADE SCAN SYSTEM AND METHOD

BACKGROUND ART

The present invention relates generally to image analysis, and more particularly, relates to tooth shade analysis tools.

In dentistry, there has been a shift in trend from a philosophy of drilling and filling to one of prevention and cosmetics. By way of example many people today are choosing to have clinical procedures done to enhance their smile and appearance. Most of these procedures involve the modification of tooth shape, alignment, and/or color.

The use of intraoral video and/or imaging systems (hereinafter "intraoral camera system") has grown rapidly in dentistry over the past few years. Such systems are widely utilized in "show and tell" settings, i.e., where the dentist can show and illustrate particular features of a patient's mouth. These intraoral camera systems are rapidly becoming key for complex diagnostic and treatment planning. Research has indicated that approximately 30% of the practicing dentists in the age group between about 35-54 own and utilize intraoral camera systems. It is expected that this percentage will increase with increased familiarity with such systems. See Dental Procedures Report, Pgs. 22-24, February 1995.

A necessary step in altering a patient's tooth color is to determine the "shade" of the existing tooth. For example, those persons seeking a whiter, brighter smile are still assessed to establish their existing tooth color so that an appropriate before and after comparison can be made. Shade determination is even more important for those persons seeking reconstructive work, since one goal of the reconstructive process is to achieve a natural appearance. Therefore, it is important to know the existing tooth shade so that it can be accurately matched with the new restoration. The dental profession utilizes standardized shade guides created by those companies which manufacture the reconstructive materials. One well-known shade guide is the Vita™ shade guide, which includes sixteen different shades. Other, less popular shade guides include those guides provided by Bioform™ and SR-Vivadent™.

These shade guides are utilized in a rudimentary fashion. The guide itself is a plastic plate with a plurality of removable color tabs that are shaped like a tooth, e.g., the front tooth. Typically, to assess a patient's tooth shade, a dentist removes one of the colored tabs and holds it up to the patient's tooth so that she can "eyeball" the closest match possible. Understandably, there are many variables to this method, some of which stem from the subjectivity of the dentist making the eyeball assessment.

Once the tooth shade is determined, the information is used relative to the particular procedure needed. In bonding or filling a tooth, for example, the composite materials required for the restoration are specified within the range of the shade guide, e.g., one of sixteen shades for the Vita™ range. More particularly, if a crown, bridge or denture is needed, the patient's shade must be determined and communicated correctly to the lab that makes the crown, bridge or denture.

The communication of shade information between the dentist and the lab is extremely important. Often there is a breakdown or failure in this communication, resulting in a poor shade match for the patient. In some cases, a particular dentist utilizes an uncommon shade guide, thereby leaving the lab technician to eyeball and convert the shade information to a Vita™ standard shade (since porcelain is often made from the Vita™ Shade guide). This too can result in improper shade matching.

The process for selecting the porcelain for a particular tooth shade illustrates the difficulty in assessing and manufacturing the correct color match. If, for example, a crown of Vita™ shade A3 is desired, porcelain is built by hand with a paintbrush onto a model of the tooth to be restored. The porcelain is built in layers on the model to achieve translucency and natural appearance. Each layer has a particular color and intensity associated with it. To generate shade A3, the technician follows a "recipe" that is given by the manufacturer Vident™, requiring a different shade for each layer of porcelain applied. If a doctor asks for a shade that is not a Vita™ standard shade, the technician typically seeks to achieve that shade by combining different porcelain shade combinations together, to increase or decrease the chroma, hue and value of the shade.

To further complicate the color-matching process, some dentists are simply not skilled in taking and determining shade information. Therefore, these dentists sometimes send their patients directly to the lab where the technician can determine the shade information. Alternatively, these dentists sometimes have a technician come to their office. In either event, there are, at times, one or more levels of subjective uncertainty injected into the correct match and determination of a patient's tooth shade. Thus, there is a need for more improvements in this area.

In one known technique, a system operator is permitted to select an image of a single area on a patient's tooth, which the system compares to a specifically corresponding image processor in a shade guide. Such techniques have drawbacks such as being intensive, time consuming, etc.

Thus, in addition to the needs discussed above, known techniques do not appear to desirably address limitations that exist in processing, communications, storage, and/or other capabilities with respect to hardware or software equipment used in shade analyzing.

SUMMARY OF THE INVENTION

In accordance with the principles of the present invention, tooth shade scan systems and methods are provided in which shade information for a restorative product for a patient's tooth is obtained. The system may capture image information for a patient's tooth and compile the image information to a database of shade guide information.

Software and/or hardware may be implemented that displays an image of the patient's tooth and displays dividers by which an operator can divide the tooth into regions of interest or into regions that correspond to major tooth regions (e.g., the incisal, central, etc.). The dividers may be displayed over an image of a patient's tooth. The dividers may be moved under operator control to allow the operator to identify the appropriate regions for which corresponding information is available from a database of shade guide information. The dividers may, for example, be lines that are fixed in reference to each other, may be parallel lines, or may have other positional relationship to each other for dividing tooth regions. The operator may be given control of the shape of the dividers (e.g., the operator may be permitted to create curves in lines used as dividers). The dividers allow the operator to identify two or more regions depending on the number and shape of the lines at the same time. Imaging equipment such as an intraoral camera may be used to obtain an image of the patient's tooth.

Once regions of interest are identified, color characteristics for those regions are obtained. Color characteristics such as valves for red, green, blue, intensity, and other characteristics may be obtained. Average values over an area, such as a major tooth region, may be used for the color characteristics. Other types of calculations may also be applied to identify a number that is representative of a color characteristic. Thus, color characteristics for several major regions (e.g., only three regions) of a tooth may be obtained.

An electronic shade guide may be provided. A database of information on tooth shades in a shade guide may be obtained. The database may contain information organized by tooth region. The information may be obtained using imaging equipment such as that which is used for imaging a patient's tooth. The same imaging equipment may be used for a patient's tooth and a shade guide to avoid discrepancies in image quality or measurement. If desired, calibration techniques may be applied to providing matching image (e.g., color) characteristics between images obtained for a patient and images obtained from a shade guide. If desired, a database of shade guide information may be distributed to dentists or technicians, or may be stored centrally for analysis of patient images at a manufacturing site. If the database is distributed, the information may be stored for local use by, for example, dentist or technicians.

Information obtained by region for a patient's tooth may be applied to the database to identify tooth shades for a restorative product to be used for the patient. Numerical values for a limited set of color characteristics may be generated for each region of a patient's tooth. A corresponding set may exist in a database of shade guide information that was generated from a tooth shade guide. The values for the patient may be applied to the database to identify tooth shades for the patient by region. The region-by-region comparison and the comparison of a limited set of color characteristics that are representative of a region as a whole, allows for quick and simple analysis and identification of tooth shades for a patient.

BRIEF DESCRIPTION OF THE DRAWINGS

Further features of the invention, its nature and various advantages will be more apparent from the following detailed description, taken in conjunction with the accompanying drawings in which like reference characters refer to like parts throughout, and in which:

FIG. 6 is a diagram of illustrative database and patient tooth shade information in accordance with one embodiment of the present invention.

DETAILED DESCRIPTION OF PREFERRED EMBODIMENTS

A database having discrete shade information for different major tooth regions allows for quick identification of appropriate tooth shades for a patient's tooth. Identification may be based on numerical comparison between values assigned to color characteristics of certain regions in a patient's tooth and color characteristics of tooth shades for specifically corresponding tooth regions in a shade guide. The use of tooth regions (e.g., whole regions, major tooth region, etc.) for tooth shade identification allows for sufficiently accurate shade identification without requiring complex and time-consuming analysis and/or comparison of images such as, comparison of bitmap images, which is highly processor intensive.

Figure 1:
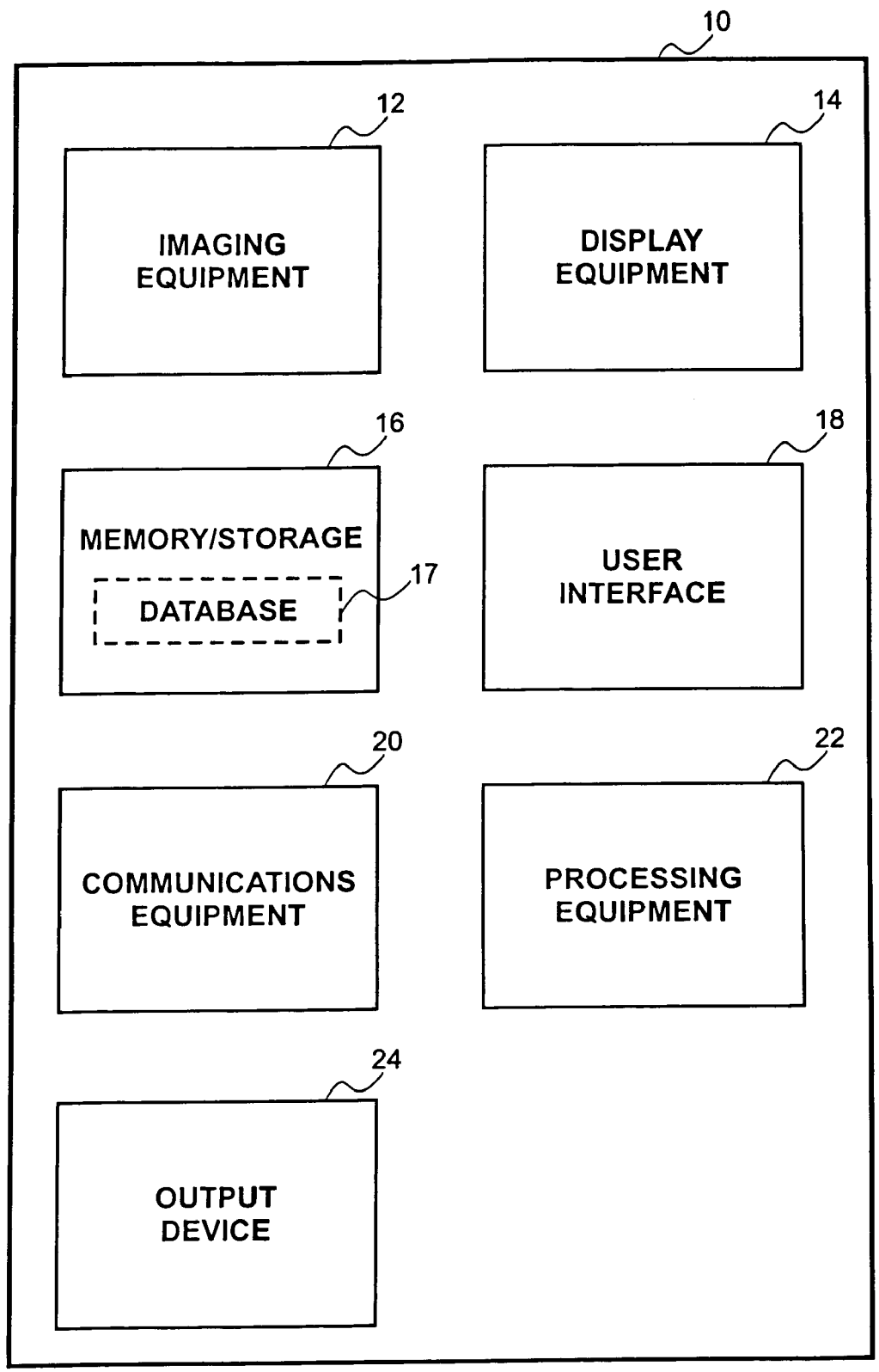
FIG. 1 is a functional block diagram of an illustrative tooth shade analyzing system in accordance with one embodiment of the present invention.

With reference now to FIG. 1, illustrative shade analyzing system 10 may be a system that is used to obtain image information (e.g., an image) of patient's tooth. System 10 may also be used to generate values for color characteristics that are sensed or determined from image information, to identify tooth shade by regions, and to perform other related activities. Shade analyzing system 10 may include imaging equipment 12, display equipment 14, memory/storage 16, user interface 18, communications equipment 20, processing equipment 22, and output device 24.

Imaging equipment 12 may be equipment for obtaining information on physical and/or color characteristics of a patient's teeth. Imaging equipment may be a digital camera (e.g., an intraoral camera). Examples of imaging equipment 12 may include Power ‰ offered by Insight of San Carlos, Calif., and Cygenascope offered by Cygnus Instruments, Inc. of Goleta, Calif. Another example is a product named VistaCam by Air Techniques of Hicksville, N.Y. Such devices may be handled devices and in some applications may include their own software, display unit, storage, and/or communications capability (e.g., communications with personal computers). Such devices may be capable of sensing brightness, color (e.g., RGB, L*, a*, b*, etc.), hue, or chroma. Other characteristics of an image or portions of an image may be also be obtained if desired.

Display equipment 14 may be equipment from which an operator may view an image of a patient's tooth and to view and use shade analyzing software features. Display equipment 14 may be a computer monitor that is operably coupled to a computer which supplies display information to the monitor. Other equipment may also be used.

Memory/storage 16 may be equipment that is used to store an electronic shade guide, to store shade analyzing software applications or other applications, store database 17 containing shade guide information (e.g., certain color characteristics of tooth shades in a shade guide by region). Values stored in the database may be categorized based on tooth regions. Memory/storage 16 may be a hard drive or other type of computer storage equipment. Other types of memory or storage are known to those skilled in the art (e.g., RAM, ROM, DVD, CD, etc.).

User interface 18 may be equipment that permits an operator to interact with shade analyzing system 10. User interface 18 may include a keyboard, a mouse, a voice recognition system, etc.

Communications equipment 20 may be equipment that permits inter-computer communications, for example, for the transfer of shade information between computers. Communications equipment 20 may include a modem, an ethernet card, a digital subscriber line interface, a cable modem, etc. Other types of communications equipment are known to those skilled in the art.

Processing equipment 22 may be a processor and/or related circuitry that may be used in analyzing and/or identifying tooth shades. Processing equipment 22 may be a central processing unit of a computer such as a personal computer that may include display equipment 14, user interface 18, memory storage 16, communications equipment 20, and/or output device 24. Processing equipment 22 may be part of a computer system that is remote from a location in which tooth image information for a patient is obtained. An individual processor or combinations of processor (e.g., remote and local) may be used in providing sufficient processing to system 10.

Output device 24 may be equipment such as a printer that provides an output of text or images for system 10. Other types of output devices are known to those skilled in the art.

System 10 may include an intraoral camera system. Examples of shade analyzing systems are illustratively shown in U.S. Pat. No. 6,305,933 B1 to Lehman and in WO 00/25696 entitled "Interactive Dental Restorative Network" published May 11, 2000, which are hereby incorporated by reference herein in their entireties. Other equivalent intraoral or digital cameras can be substituted if desired. It is instead possible to use a color imaging device or spectrophotometer, if desired, to collect the color information from the patient's tooth and the reference shade guides. In all these devices, it is preferred to include an isolation sleeve or other stray light-shielding device so that the most accurate images of the color of the tooth can be obtained. These are shown for example in U.S. Pat. Publication No. 20030148243 of Kerschbaumer et al, which was filed Dec. 24, 2002 which is incorporated herein by reference in its entirety.

Figure 2:
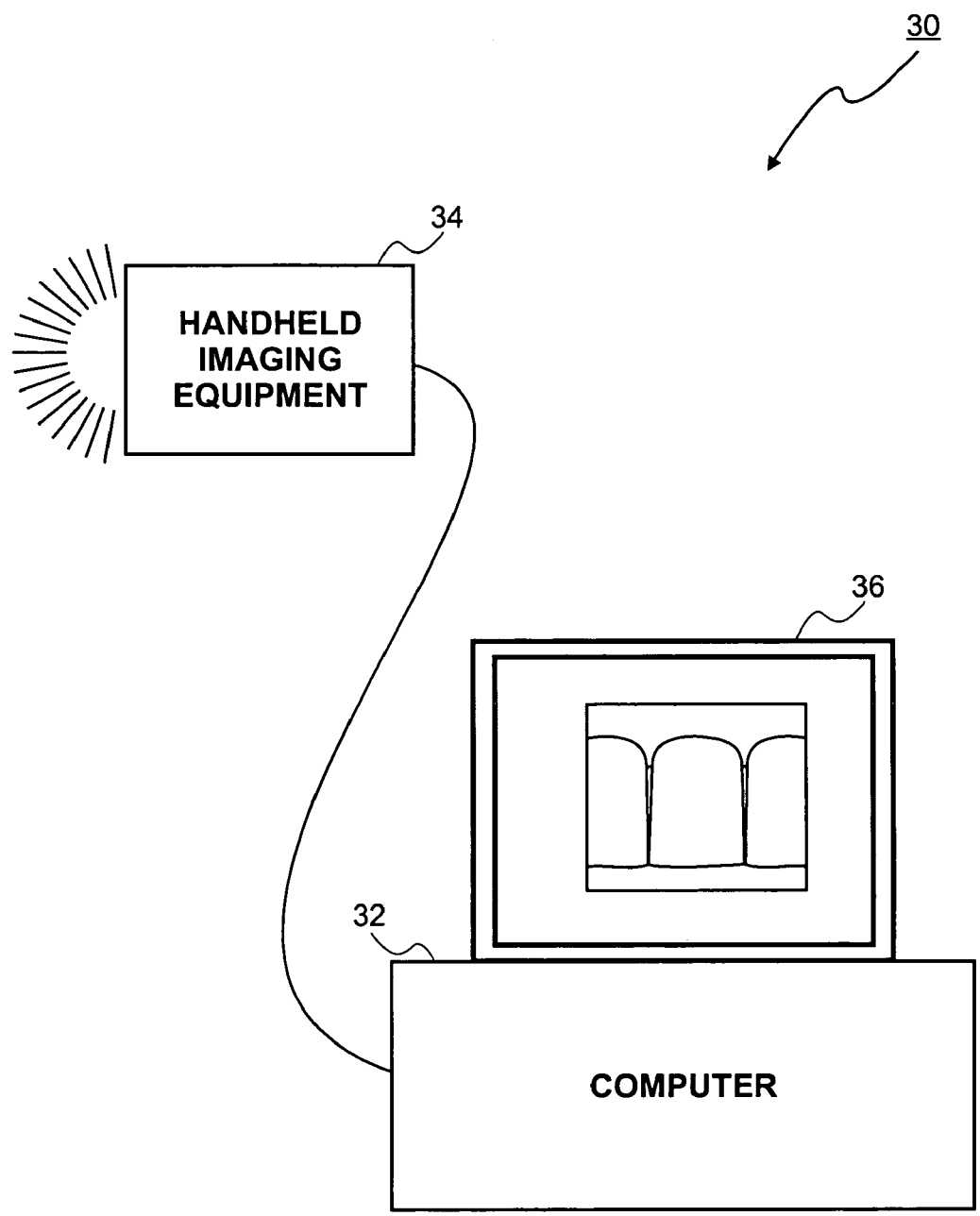
FIG. 2 is a functional block diagram of a per based shade analyzing system in accordance with one embodiment of the present invention.
Figure 3:
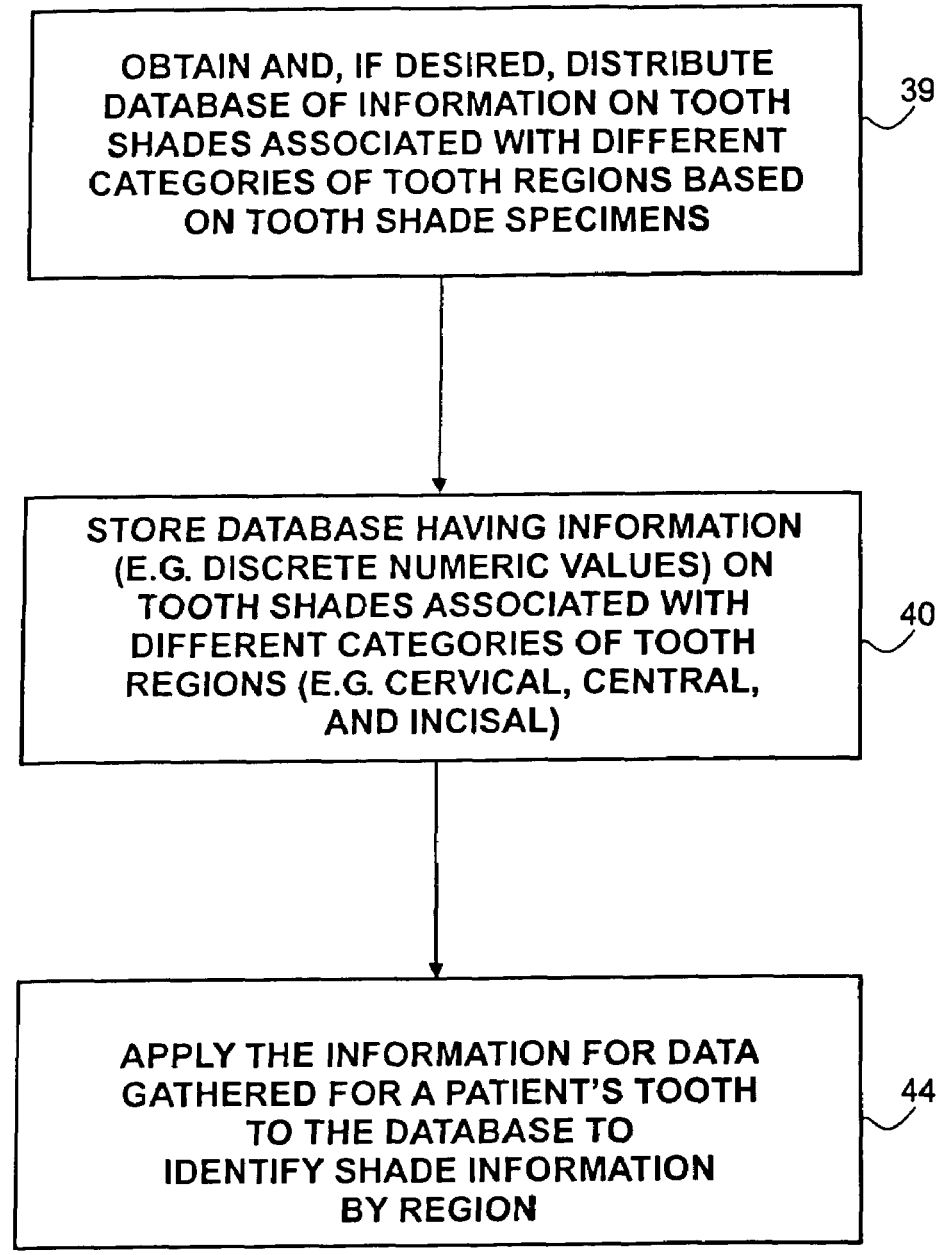
FIG. 3 is a flow chart of illustrative steps involved in analyzing tooth shades using a database of region specific tooth shade information in accordance with one embodiment of the present invention.
Figure 4:
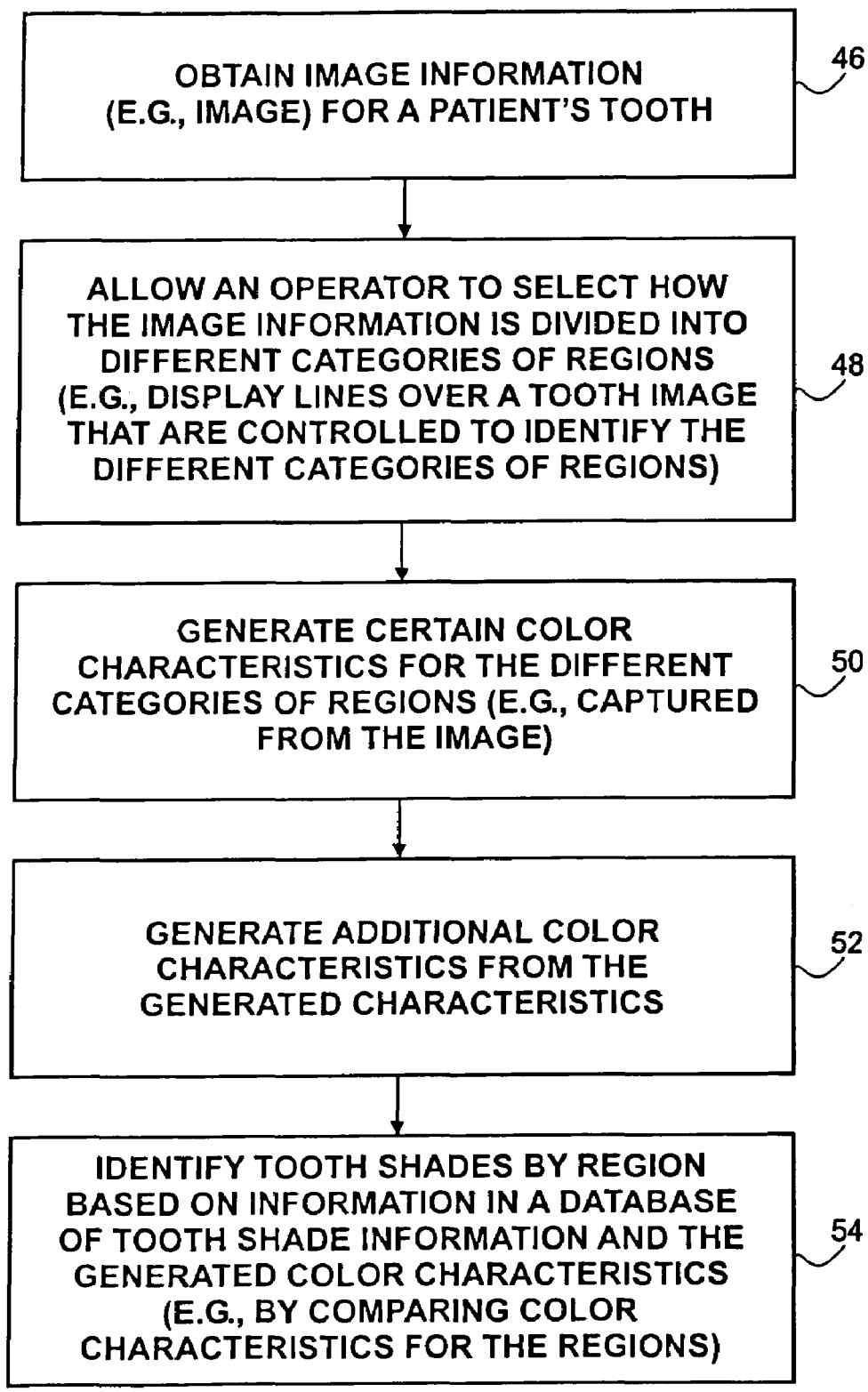
FIG. 4 is a flow chart of illustrative steps involved in identifying tooth shades for a patient's tooth in accordance with one embodiment of the present invention.

An example of a shade analyzing system is illustratively shown in FIG. 2. With reference now to FIG. 2, shade analyzing system 30 may include sufficient hardware and software for identifying shade information for a patient's tooth from a shade guide. System 30 may include personal computer 32 and hand-held imaging equipment 34. System 30 may be a personal computer that is configured with sufficient communications equipment, memory/storage, processing equipment, space display equipment, user interface capabilities, and/or output device capabilities, or configured with combinations thereof. System 30 may include display equipment, such as, computer monitor 36. Handheld imaging equipment may be imaging equipment that is used to capture shape and color information for a patient's tooth. An image of a patient's tooth may be displayed on monitor 36. Information generated from the image may be analyzed by computer 32 to identify shades from a shade guide that are to be used for a restorative product or service that is to be provided to a patient. Information that is generated from the image may be compared against a shade guide database to identify appropriate shades for a patent's tooth. Shade information for a current patient's tooth may be displayed on a user interface to allow inspection of the information by an operator. If desired, shade information for a current patient's tooth may be sent to a remote site for tooth shade analysis.

The techniques that are illustratively described herein (e.g., in FIGS. 3-6) may be implemented using the illustrative systems of FIGS. 1 and 2. Other suitable platforms or components may also be applicable.

Tooth shades for tooth restoration may be identified by region, rather than by pixel or by tooth (i.e., a tooth as a whole). For example, with reference now to FIG. 3, at step 39, a database of information on tooth shades from tooth shade specimens (i.e., physical specimens in a shade guide) may be obtained and if desired distributed to dentists or technicians. The database of information may be obtained in a way that is calibrated with respect to techniques used to obtain the information for patient information. For example, the same imaging equipment may be used both for the development of the database and for obtaining intraoral images of patients. The information in the database may be on tooth shades, wherein the shades are associated with different categories of tooth regions (e.g., spatially different and/or mutually exclusive regions). Thus, for example, the database may have a set of color characteristics for each shade in the shade guide that is available for the incisal region of a tooth. At step 40, the database may be stored locally at a dentist or technician's office, or at some other appropriate site for analysis. The database may include an electronic shade guide that is provided by a manufacturer of a restorative product, may include images of shade guides by tooth region, or may include information providing detailed color characteristics of shade guides. Such information may have been obtained using the same or similar imaging equipment that is used to obtain tooth information for a patient or may be obtained with information to compensate for differences in imaging characteristics of different imaging equipment being used. The tooth regions may be general tooth regions such as the cervical, incisal, and central tooth regions.

Each numerical value that is stored in the database may be strictly associated with one of the tooth regions and may represent a certain color characteristic of a tooth shade for that particular region. The use of values for whole regions should consume less memory than is used by conventional systems, should speed up the tooth shade analysis process, and has been found to provide desired levels of accuracy.

At step 44, patient information is applied to the database to identify tooth shade information for a patient. Information from the database may be compared with information gathered from different regions of a patient's tooth to identify appropriate shades to be used for the different regions of the patient's tooth. The comparison may involve a comparison of numerical values.

Control over identifying regions of interest of a patient's tooth for which corresponding information exists in the database may be under an operator's control. For example, with reference now to FIG. 4, an operator may obtain image information of patient's tooth using imaging equipment such as those illustratively mentioned above. At step 48, an operator may be given control over how the image information will be divided into different categories of regions for use in the shade analysis process.

An operator may be given control to select the regions (e.g., three regions at approximately the same time (e.g., at the same time).

For example, an image showing the patient's tooth may be displayed on display equipment (e.g., display equipment 14 of FIG. 1). Two or more lines may be displayed over the image. The lines may be parallel lines and/or lines that are fixed in distance in relation to each other. The position of the lines in the image may be under operator control to allow the operator to selectively identify the different categories of regions (e.g., incisal, central, and cervical). The lines should have characteristics that are sufficient to allow an operator to selectively identify (e.g., simultaneously identify) the categories of regions (e.g., only three categories) on the patient's tooth for which database information exists. If desired the operator may be given control over the shape of the lines (e.g., to curve the line at certain points) to select appropriate divisions more accurately.

While this method can be used to identify any number of regions on the tooth, it has been found that the three regions mentioned above are the most preferred. These areas have different shapes and provide different functions to the tooth so that they have slightly different colors for those reasons. Also, it is of greater importance to color match more accurately the patient's teeth that are the most visible to others. These are basically the front four teeth on the top and bottom of the patient's jaws. The accurate matching of color for a rear molar is much less critical since it is not readily viewed by others. In those cases, a single color for the entire tooth based on an average of the regions is often sufficient.

At step 50, certain color characteristics for the different categories of regions (selectively identified by the operator) may be generated based on the image information and based on how the user divided the image information (e.g., captured from the image based on where two parallel lines dividing the patient's tooth into the incisal, central, and cervical regions were placed). The color characteristics may for example be the Red, Green, and Blue (RGB) characteristics of each region.

At step 52, additional color characteristics may be generated from the color characteristics that were generated at step 50. For example, one or more algorithms may be applied to RGB values to obtain additional color characteristics such as the C.I.E. L*, a*, and b* values. C.I.E. stands for Commission Internationale de L'Eclairage, which is an international body that sets color measurement standards. Algorithms for converting RGB values to L* (brightness), a* (measure of Red-Green), and b* (measure of Blue-Yellow) are known to those skilled in the art.

At step 54, tooth shades are identified by region based on information in a database of tooth shade information (e.g., a database such as that described in connection with FIG. 3) and based on the color characteristics that are generated. A tooth shade for a region of a patient's tooth may be identified by comparing some or all of the color characteristics that were generated for that region of the patient's tooth with corresponding color characteristics for tooth shades in the database that are associated with that same region (e.g., regions that spatially correspond).

The process may be repeated and the shade information may be communicated to a manufacturing site for production of appropriate restorative products.

Figure 5:
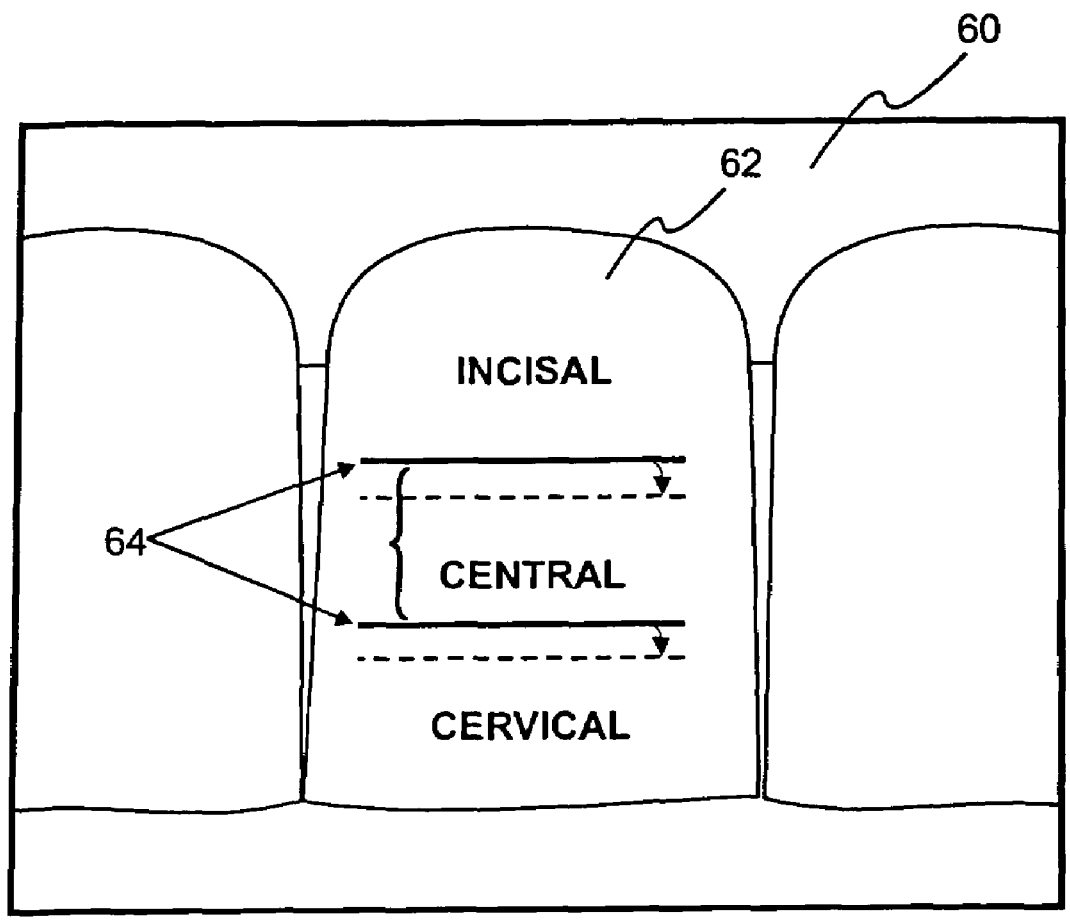
FIG. 5 is a diagram of an illustrative graphical user interface in a shade analyzing system in accordance with one embodiment of the present invention.

As mentioned above, image information may be divided using two lines (e.g., two parallel lines). An example of a technique for implementing processes described herein is illustratively shown in FIG. 5. Other techniques may also be implemented if desired. With reference now to FIG. 5, image 60 is an intraoral image of a patient's month that may be displayed on display equipment of a shade analyzing system. Image 60 may be displayed within a software window that may include software tools that the operator may select for use in the tooth shade analysis process. The object in image 60 that is currently of interest to the operator may be tooth 62. Lines 64 may be displayed over image 60. Lines 64 may be used to tooth 62 into three regions. The three regions may the incisal, central, and cervical regions of the tooth. Movement and location of the lines 64 may be under operator control to allow the operator to selectively identify where the desired regions are located on the patient's tooth 62. An operator may be given control over both horizontal and vertical movement of lines 64. The distance between lines 64 may be a fixed distance or may be a distance that is also under the control of the operator. If desired, the shape of lines 64 (e.g., curvature) may also be under operator control. Once the operator has moved lines 64 to a desired location, the operator may make a selection to indicate to the shade analyzing system that the lines are in a location that divides tooth 62 into regions for which a database of tooth shade information exists. In response, certain color characteristics for the regions may be captured from image 60 to generate discrete numerical values for the color characteristics for each region as a whole (e.g., RGB average values for each region). Additional color characteristics may also be generated based on the color characteristics that have already been generated (e.g., L*, b*, and a*). The additional color characteristics may also be generated for each region as a whole (e.g., average values for L*, b*, and a* for each region).

Color characteristic values that are generated for the tooth from image information or sensed by imaging equipment may provide a discrete set of values that can be easily and quickly compared with information in the tooth shade database to identify appropriate tooth shades for each region of the patient's tooth. For example, with reference now to FIG. 6, table 70 is a table that illustratively shows values that were generated for the incisal, central and cervical regions of a patient's tooth. The values that are shown in the table were randomly inserted and are not meant to represent actual values. The values that are generated for the regions of interest are RGB values and L*, a*, and b* values. Other major regions of interest as appropriate may also be used for tooth shade analysis.

Table 72 is representative of a tooth shade database. Table 72 is shown to include values for certain color characteristics (e.g., average value for RGB and L*, b*, and a* for a region). Information in Table 72 is divided by association with different categories such as different tooth regions of interest, e.g., the incisal, central, and cervials (as shown). For each category, there exists a range of tooth shades and values for color characteristics for each of the tooth shades. The tooth shades correspond to shades in a shade guide and as mentioned above, the values for the color characteristics may have been captured from the shade guide.

Values from table 70 may be applied to table 72 to identify appropriate shades for the regions of interest for the current patient's tooth. If desired, some or all of the color characteristics (e.g., RGB, L*, b*, a*, etc.) may be used in the analysis. Various algorithms for determining shades may be used. Algorithms such as linear fit, least squared fit, or other algorithm for comparing multiple values may be used. Also, if the color characteristics for a patient fall between two shades, some of interpolation may be applied to the two shades to produce an additional shade for the patient's tooth that suitably fits the generated color characteristics for that patient.

The value for the color characteristics is primarily discussed herein as average value. However, techniques other averaging may also be sued to assign a certain characteristic to a region.

It is to be understood that the invention is not to be limited to the exact configuration as illustrated and described herein. Accordingly, all expedient modifications readily attainable by one of ordinary skill in the art from the disclosure set forth herein, or by routine experimentation there from, are deemed to be within the spirit and scope of the invention as defined by the appended claims.

What is claimed is:

1. A method for identifying tooth shades, comprising:
   storing a database of information including at least three categories corresponding to different tooth regions, and for each category, the database including a set of values that represent tooth shades in that corresponding tooth region;

obtaining an image of a patient's tooth;

displaying two lines over the image; moving the location of the lines under operator control to selectively identify the regions on the patient's tooth;

generating values for certain color characteristics of the selectively identified regions of the patient's tooth; and identifying tooth shades for each of the selectively identified regions of the patient's tooth by comparing the values generated from each region with the set of values stored in the database for the corresponding tooth region and selecting the closest color matching values as the identified tooth shades for each region.

2. The method of claim 1 wherein the storing comprises storing numerical values in categories corresponding to cervical, central, and incisal tooth regions.

3. The method of claim 2 wherein the moving comprises moving the location of the lines under operator control to selectively identify the cervical, central, and incisal regions on the patient's tooth.

4. The method of claim 1 wherein the displaying comprises displaying two lines that are parallel.

5. The method of claim 1 wherein the displaying comprises displaying two lines that are fixed in location in relation to each other.

6. The method of claim 1 wherein the identifying comprises comparing certain color characteristics for each of the selectively identified regions with the same color characteristics for corresponding categories in the database.

7. The method of claim 1 wherein the identifying comprises identifying tooth shades by the tooth regions for which categories exist in the database.

8. A system for identifying tooth shades, comprising:

a database of information including at least three categories corresponding to different tooth regions, and for each category, the database including a set of values that represent tooth shades in that corresponding tooth region;

computer equipment that is configured to display an image of a patient's tooth, to display two lines over the image, to move the location of the lines under operator control to selectively identify the regions on the patient's tooth, to generate values for certain color characteristics of the selectively identified regions of the patient's tooth, wherein the system is configured to compare the values generated for each of the regions with the set of values stored in the database for the corresponding tooth region in order to select the closest color matching values as the identified tooth shades for each region.

9. The system of claim 8 wherein the database comprises numerical values in categories corresponding to cervical, central, and incisal tooth regions.

10. The system of claim 8 wherein the equipment is configured to move the location of the lines under operator control to selectively identify the cervical, central, and incisal regions of the patient's tooth.

11. The system of claim 8 wherein the equipment is configured to display two lines that are parallel.

12. The system of claim 8 wherein the equipment is configured to display two lines that are fixed in location in relation to each other.

13. The system of claim 8 wherein the system is configured to compare certain color characteristics for each of the selectively identified regions with the same color characteristics for corresponding categories in the database.

14. The system of claim 8 wherein the system is configured to identify tooth shades by the tooth regions for which categories exist in the database.

* * * * *